(12) United States Patent
Brasile

(10) Patent No.: US 9,232,784 B2
(45) Date of Patent: Jan. 12, 2016

(54) METHODS AND COMPOSITIONS TO MODIFY THE IMMUNOGENICITY OF A VASCULARIZED ORGAN OR TISSUE

(71) Applicant: Orgamend, Inc., Albany, NY (US)

(72) Inventor: Lauren Brasile, Albany, NY (US)

(73) Assignee: Breonics Inc., Albany, NY (US)

( * ) Notice: Subject to any disclaimer, the term of this patent is extended or adjusted under 35 U.S.C. 154(b) by 0 days.

(21) Appl. No.: 14/072,311

(22) Filed: Nov. 5, 2013

(65) Prior Publication Data

US 2014/0220548 A1  Aug. 7, 2014

Related U.S. Application Data

(60) Provisional application No. 61/722,507, filed on Nov. 5, 2012.

(51) Int. Cl.
| | |
|---|---|
| *A61K 38/39* | (2006.01) |
| *A61K 35/44* | (2015.01) |
| *A01N 1/02* | (2006.01) |
| *A61L 27/22* | (2006.01) |
| *A61L 27/36* | (2006.01) |
| *A61L 27/38* | (2006.01) |

(52) U.S. Cl.
CPC .............. *A01N 1/0226* (2013.01); *A61K 35/44* (2013.01); *A61K 38/39* (2013.01); *A61L 27/227* (2013.01); *A61L 27/3633* (2013.01); *A61L 27/3683* (2013.01); *A61L 27/3808* (2013.01)

(58) Field of Classification Search
None
See application file for complete search history.

(56) References Cited

U.S. PATENT DOCUMENTS 5,643,712 A * 7/1997 Brasile ............................ 435/1.2

* cited by examiner

*Primary Examiner* — Karlheinz R Skowronek
*Assistant Examiner* — Roy Teller
(74) *Attorney, Agent, or Firm* — Heslin Rothenberg Farley and Mesiti, PC

(57) ABSTRACT

Disclosed herein is an RGD-enriched solubilized extracellular matrix composition derived from endothelial cell culture that can be used to modify the immunogenicity or thrombogenicity of an organ intended for transplant. The RGD-enriched solubilized extracellular matrix composition is applied to the lumen of the vasculature of the organ, thereby placing a barrier between the antigens on the lumenal surfaces of the transplanted organ and the blood of the recipient.

14 Claims, 3 Drawing Sheets

METHODS AND COMPOSITIONS TO MODIFY THE IMMUNOGENICITY OF A VASCULARIZED ORGAN OR TISSUE

CROSS REFERENCE TO RELATED APPLICATIONS

This application claims the priority of U.S. provisional application Ser. No. 61/722,507 filed Nov. 5, 2012, the contents of which are herein incorporated by reference into the present application.

FIELD OF THE INVENTION

The invention relates generally to transplantation of organs and in particular to a method for reducing the immunogenicity of a graft intended for transplant.

BACKGROUND

Organ transplantation is the therapy of choice for endstage organ failure. In the case of kidney failure, for example, transplantation provides for increased life expectancy, enhanced quality of life, and is more cost-effective than maintaining patients on hemodialysis. In the case of extrarenal organs, transplantation is life-saving since no equivalent to hemodialysis exists for these organs.

Rejection of the transplanted graft is an immunological response in which the recipient's immune system recognizes the graft as "foreign" and attempts to eliminate the transplanted graft. Part of the response involves binding of the recipient's antibodies to the donor's vascular endothelial cells lining the blood vessels within the transplanted graft. Antibody deposition leads to the activation of the complement cascade which mediates a cytotoxic phenomenon which can directly damage or kill the endothelial cells.

In addition the complement cascade leads to the activation of the endothelial cells which causes subsequent change in the anticoagulant environment. More specifically, the vascular endothelium normally provides a nonthrombogenic surface; however, when activated by the immune system during the rejection process, the endothelial lining transforms into a procoagulant environment. The resultant prothrombotic (thrombogenic) surfaces then attract polymorphonuclear cells and platelets, resulting in the endothelium being damaged and causing separation from the underlying substratum, and ultimately, severe thrombosis of the graft.

The standard approach to mitigating the rejection process is to treat the transplant recipient daily with an immunosuppressive regimen. However, currently immunosuppressive regimens are systemic; i.e., in addition to suppressing immune function against the transplanted graft, immune function which protects the recipient from other processes (such as infections) is suppressed. Further, the currently available immunosuppressants may cause substantial non-specific, toxic effects on cell types other than cells of the immune system.

U.S. Pat. No. 5,643,712 describes a method for treating and rendering grafts nonthrombogenic and substantially nonimmunogenic using an extracellular matrix coating. Disclosed is a material that can be applied to the luminal surface of the blood vessels of a vascularized tissue or organ.

SUMMARY OF THE INVENTION

In one aspect, the present invention relates to a composition and method for treating luminal surfaces of the vasculature of a tissue or organ for the purpose of rendering the tissue or organ substantially non-immunogenic and non-thrombogenic, the method comprising (a) establishing the organ or tissue in a warm perfusion system capable of supporting the near normal oxidative metabolism of the organ or tissue; (b) perfusing the organ or tissue with a non-blood perfusion solution, containing a component of the citric acid cycle selected from coenzyme A, FAD, DPN, cocarboxylase and TPN, for a time sufficient for vasodilation to occur; and (c) introducing into the organ or tissue a solubilized sonicated extracellular matrix preparation in an amount sufficient to substantially coat the luminal surfaces of the vasculature of the organ or tissue, wherein said solubilized sonicated extracellular matrix preparation renders the organ or tissue non-thrombogenic, and substantially nonimmunogenic.

In one aspect the invention relates to an Arg-Gly-Asp (RGD)-enriched solubilized extracellular matrix comprising extracellular matrix protein from cultured endothelial cells, wherein said protein in said matrix is in the amount of 1-5 mg/ml and has an RGD absorbance at 450 nm of 0.3 to 0.7, and wherein said extracellular matrix has a fragment size of less than 2 microns.

In a related aspect, the invention relates to a method for making an RGD-enriched solubilized extracelluar matrix composition, the method comprising culturing endothelial cells to confluence in an endothelial cell culture medium comprising ascorbic acid, retinoic acid and a glucose concentration in the range of about 1 to about 10 mg/ml; (b) decellularizing the culture to remove endothelial cells but leave the intact extracellular matrix; (c) solubilizing the extracellular matrix by acidification in the cold; (d) disrupting the solubilized extracellular matrix to ensure fragment size of <2 microns; and (e) recovering the RGD-enriched solubilized extracellular matrix, wherein said solubilized extracellular matrix comprises extracellular protein from endothelial cells in the amount of 1-5 mg/ml, an RGD absorbance at 450 nm of 0.3 to 0.7 and a fragment size of less than 2 microns. In one embodiment, the concentration of ascorbic acid in the culture medium is about 20 μg/ml, the concentration of retinoic acid is about 152 μg/ml and the glucose concentration about 5 mg/ml.

DETAILED DESCRIPTION OF THE INVENTION

Figure 1:
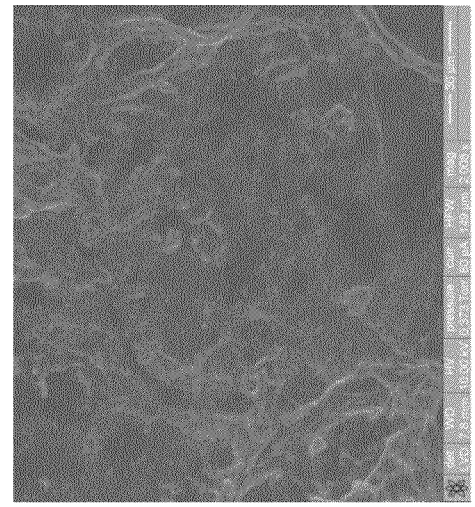
FIGS. 1a and b are electron micrographs of vascular endothelial cells (VECs) lining the luminal surface of the renal arcuate artery before (a) and after (b) administration of the composition of the invention.
Figure 1:
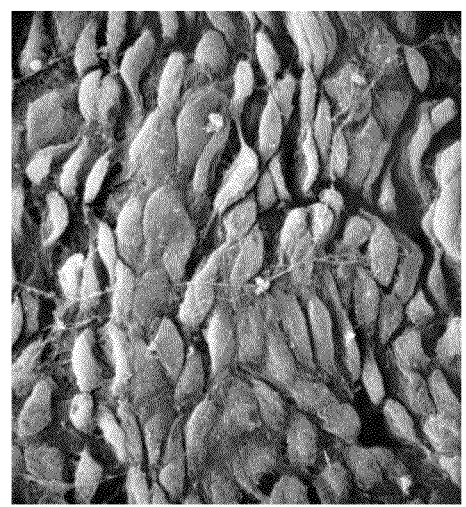
Figure 2:
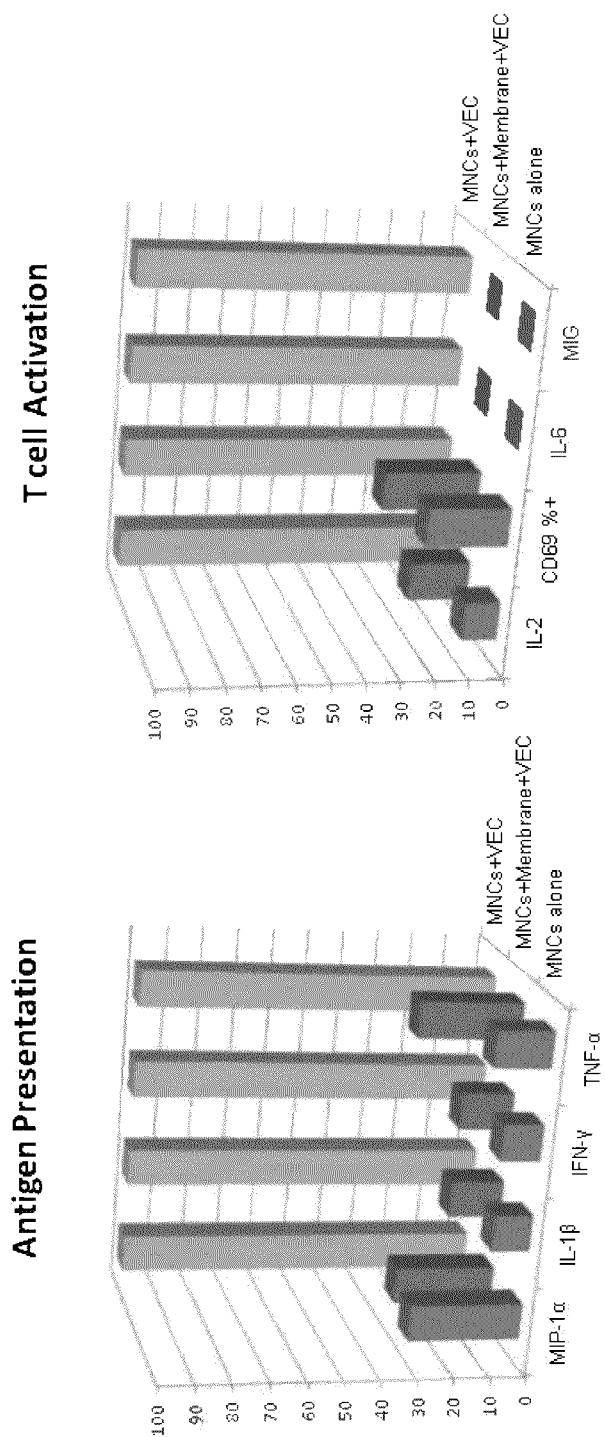
FIG. 2 shows the results of experiments to evaluate the effect of ECM on antigen presentation and T-cell activation.
Figure 3:
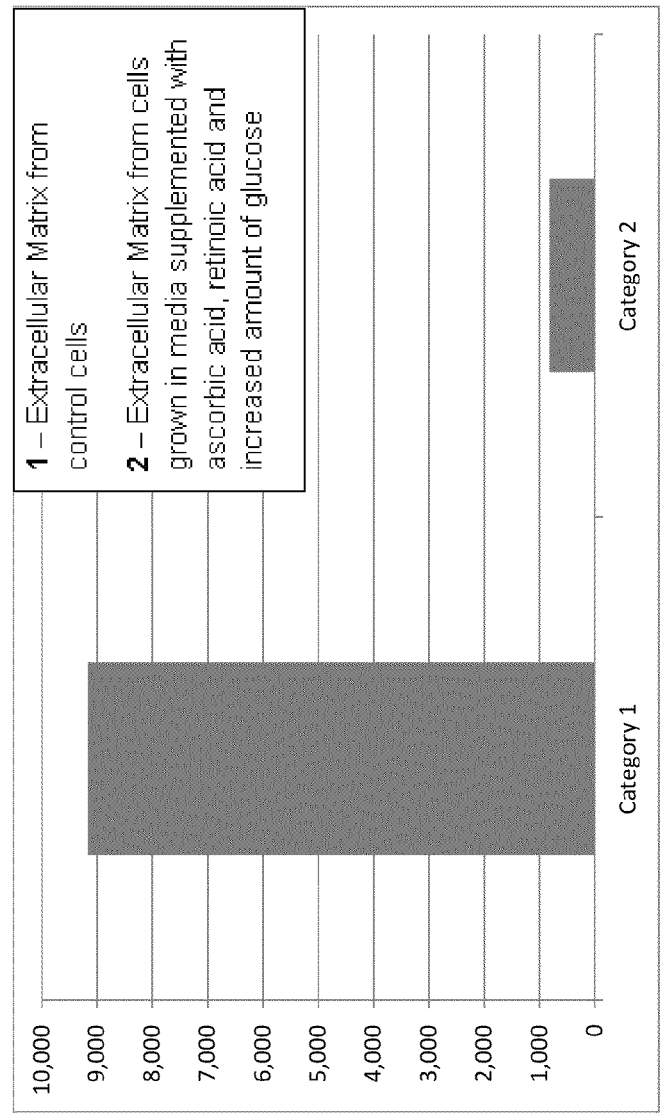
FIG. 3 shows binding of an anti-β1 integrin antibody to a monolayer of vascular endothelial cells as an indication of the effectiveness of the ECM preparation of the invention compared to prior preparations.

All patents, published patent applications, and non-patent references cited herein, including U.S. Pat. Nos. 6,642,045, 6,582,953 and 6,375,613 are hereby incorporated by reference in their entirety into the subject application.

In the description that follows, certain conventions will be followed as regards the usage of terminology.

The term "organ, tissue or section of anatomy" refers to an excised viable and whole section of the body to be maintained as such in the EMS of this invention, and refers to an intact organ including, but not limited to, a kidney, heart, liver, lung, small bowel, pancreas, brain, eye, skin, limb or anatomic quadrant. The term "organ product" refers to any substance generated as the result of the secretory function of an organ, frequently a fluid, for example, bile from liver, urine from kidneys, but also includes mechanical functions such as kidney filtration or heart pumping.

The terms "perfusion solution" and "perfusate" are used interchangably and refer to a non-blood buffered physiologic solution that provides means for reestablishing cellular integrity and function in organs which may have experienced ischemic damage prior to or during isolation and further, enables an organ or tissue to be maintained at a near normal rate of metabolism.

The term "non-blood" is intended to exclude perfusates comprising substantially whole blood or its individual components. The perfusion solution of the present invention may, however, contain a minimal amount of whole blood or a blood component, for example, red blood cells, serum or plasma.

The terms "near normal rate of metabolism" and "near normal metabolic rate" are defined as about 70-100% of the normal rate of metabolism for a particular organ as determined by measuring and evaluating whether functional characteristics of an organ, such as those described in U.S. Pat. No. 5,699,793, are within the range associated with normal function for that particular organ. Examples of functional characteristics include, but are not limited to, electrical activity in a heart as measured by electrocardiogram; physical and chemical parameters of organ product, for example, oxygen consumption and glucose utilization which can be ascertained from perfusate concentrations; pancreatic enzymes; heart enzymes; creatinine clearance and filtration functions, and specific gravity of urine and so on.

The present invention provides an optimized material and method for modifying the immunogenicity and thrombogenicity of tissues and organs. The immunocloaking treatment protects transplanted tissues and organs from allorecognition that normally occurs when circulation of the recipients' blood through the implanted tissue or organ is resumed. Recipient immune cells in circulating blood recognize the transplanted tissue as foreign. The interface of the subsequent immune-mediated rejection is the vascular endothelium, i.e. the point where the recipient's immune cells meet donor tissue. The vascular endothelium is the target of immune rejection whether the response is immediate, accelerated, acute or even chronic. The ability to adequately modify the immunogenicity of the vasculature within an allograft prevents the immune rejection cascade.

Immunocloaking Material

U.S. Pat. No. 5,643,712 describes an extracellular matrix material produced by culturing corneal endothelial cells in flasks. When the corneal endothelial cells reached a confluent state, that is, when the entire surface of the culture vessel was covered with cells with tight cell junctions, the flasks were decellularized non-enzymatically to remove the corneal endothelial cells while leaving the extracellular matrix intact. The extracellular matrix was then solubilized by acidification in the cold. When acidified solubilized extracellular matrix was neutralized at normothermic temperature, the solubilized extracellular matrix components re-polarized to form a reconstituted extracellular matrix. It was proposed that the neutralized extracellular matrix components could be applied to the luminal surfaces of the vasculature during near-normothermic perfusion to result in a modified luminal vascular surface that was nonimmunogenic and nonthrombogenic.

Disclosed herein is an improved immunocloaking material. The extracellular matrix preparation produced by the cultivation of corneal endothelial cells was optimized by culturing endothelial cells in a tissue culture medium supplemented with a combination of ascorbic and retinoic acids and an increased carbohydrate concentration. The resulting extracellular matrix that is produced using the enhanced medium contains a higher concentration of proteins and an increased concentration of Arg-Gly-Asp (RGD) sequences in the proteins. RGD facilitates binding to the surface of the vascular endothelial cells via their respective adhesion molecules. The extracellular matrix produced by the present invention predominantly consists of a network of molecules with self-assembly consisting of a laminin template for the scaffolding, glycoproteins, proteoglycans, carbohydrate moieties, vimentin, fibronectin, elastin and a network of collagen fibrils. The ability of the extracellular matrix to effectively bind to the luminal surfaces of the vascular endothelial cells lining the vasculature is dependent upon interactions that are affected by the number and intensity of the adhesions between the vascular endothelial cell surface integrins and specific peptides in the polymerized extracellular matrix. A number of surface integrins facilitate the vascular endothelial cell binding to the extracellular matrix of the present invention. However, the $\beta 1$ integrin sub-family represents a major class of integrins that interact with a number of the individual components of the extracellular matrix of the present invention, including laminins and type IV collagen. These vascular endothelial cell integrins provide for the anchorage of the extracellular matrix components that facilitates the re-assembly of the solubilized and neutralized material that provides the immunocloaking membrane. (132,133) In vitro studies using ECM prevented cell penetration into the engineered tissues while also providing a compatible environment for confluent cell populations.

Cultivation of Corneal Endothelial Cells (CEC)

In one embodiment, the immunocloaking material of the invention is derived from corneal endothelial cells (CEO), which were obtained as follows. Corneas were dissected from the intact orbit maintaining sterility. The luminal surface was treated with a digestive enzyme and incubated at 37° C. for 20 minutes. The digestate was collected, washed and resuspended in tissue culture media. The isolated corneal endothelial cells were then placed in tissue culture flasks and fed every three days until confluent. Control cultures were maintained in Medium 199 supplemented with 10% serum and Fibroblast Growth Factor-basic (FGF) (5 ng/ml). Experimental cultures were cultured in the same medium as control cultures, but supplemented with ascorbic acid (20 ug/ml), retinoic acid (152 µg/ml), glucose (5 mg/ml), Vascular Endothelial Growth Factor (VEGF)(5 ng/ml), Epithelial Growth Factor (EGF)(5 ng/ml) and Insulin-like Growth Factor (0.5 ng/ml) (referred to hereinafter as the AA/RA-supplemented media). As shown in Table 1, culture of CECs in the AA/RA-supplemented media resulted in significantly shorter times to confluence and a shortened population doubling time.

TABLE 1

| Corneal Endothelial Cell (CEC) Growth Curves | | |
|---|---|---|
| Primary CEC cultures | Control Media | Present Invention |
| Time to Confluence | 7 days (+/−2) | 2 days (+/−0.5) |

Without wishing to be bound by theory, it is thought that retinoic acid functions by accelerating the induction of corneal endothelial cell differentiation and by contributing to increased extracellular matrix secretion. This increased secretion of extracellular matrix is in part attributable to increased laminin, collagen type IV and glycosaminoglycans synthesis. The higher concentration of glucose provides a positive effect on the metabolic rate and the corresponding rate of synthesis. Ascorbic acid provides an additive effect on the synthesis of the various components of the extracellular matrix by the corneal endothelial cells.

While a range of glucose can be used, most commonly used tissue culture media contain a normal glycemic concentration of 5.5 mM (1 g/L). Ascorbic acid is not usually included in the formulations of common tissue culture media and retinoic acid is rarely included.

Secreted Extracellular Matrix

Extracellular matrix from the corneal endothelial cells grown in the control media was acidified, incubated and scraped from the surface of the tissue culture vessel. Similarly, the extracellular matrix produced by the corneal endothelial cells grown to confluence in the AA/RA-supplemented media was also recovered by acidification. When harvested, the solubilized extracellular matrix is not uniform and may contain large fragments that are not easily broken apart. In order to administer the solubilized extracellular matrix in a way that does not obstruct or clog smaller blood vessels and to also result in a uniform layering of the immunocloaking matrix membrane it is necessary to further fragment the solubilized material. The large fragments can be further reduced in size by several methods. These methods include sonification, pepsin digestion and guanidine-HCl treatment. Sonification entails fragmentation that results in smaller particles sizes ranging from 5-20 nanometers. Care is needed to limit the unfolding of the protein and the formation of amyloid-like structures. Pepsin digestion of the large fragments into peptides is effective in the acidic environment of the soluble extracellular matrix mixture. Guanidine-HCl fractionates the large protein fragments in the acidified solubilized extracellular matrix and allows for the re-polymerization when neutralized and at near-normothermic temperatures.

Characteristics of the Immunocloaking Extracellular Matrix

The extracellular matrix produced by the corneal endothelial cells grown in AA/RA-supplemented media contains a significantly higher concentration of protein in comparison to the control preparations produced by the method of U.S. Pat. No. 5,643,712 as measured using a standard Lowry assay (Table 2). The extracellular matrix was decellularized, acidified and then treated to render the solubilized material into small fragments. The protein concentration was determined in batch of extracellular matrix manufactured by the method and process of the present invention (n=10) and compared to the material produced by the method of U.S. Pat. No. 5,643,712A.

Using an antibody to the peptide sequence Arg-Gly-Asp (RGD) in an indirect immunofluorescence assay, the extracellular matrix produced by the method and process of the present invention results in an immunocloaking membrane that contains significantly increased RGD in comparison to control extracellular matrix produced by the method of U.S. Pat. No. 5,643,712A (Table 2).

Confluent cultures of corneal endothelial cells were decellularized and the exposed extracellular matrix was tested by incubating the exposed membrane with an antibody to the RGD-containing peptides after first treating the decellularized surface with a blocking step consisting of 5% BSA for one hour. The matrix membranes were then washed with PBS and then a secondary fluorescein tagged antibody was applied and incubated for an additional one hour. Following incubation, the matrix membrane was again washed and the absorbance at 450 nm was determined. The results are listed in Table 2.

TABLE 2

Analysis of the immunocloaking extracellular matrix

| | Control Extracellular Matrix | Present Invention |
|---|---|---|
| Protein concentration (ug/ml) | 518 (+/−172) | 4,918 (+/−1,425) |
| RGD* | 0.1 (+/−0.05) | 0.5 (+/−0.03) |

*absorbance at 450 nm

Alternatively, an optimized immunocloaking membrane can be obtained by isolating the naturally occurring sub-endothelial cell extracellular matrix from human blood vessels. In particular, endothelial cells from human umbilical cord veins (HUVEC) and arteries can be the source of a rich extracellular matrix that displays the same immunocloaking properties as the optimized extracellular matrix produced by corneal endothelial cells in culture. The native extracellular matrix can be obtained by decellularization of the vascular endothelium that lines the luminal surface of blood vessels in vivo. The extracellular matrix can then be harvested by acidifying the blood vessel lumen and solubilizing the sub-endothelial matrix. Following the collection of the native extracellular matrix, the material can be neutralized, stored and re-polymerized.

Fragmentation of the Extracellular Matrix

The isolated extracellular matrix material, whether from the culture of corneal endothelial cells or native blood vessels must be processed to ensure that the components are fragments small enough to be applied to complex vasculature without clogging the microvessel beds. To adequately disperse the solubilized extracellular matrix constituents, it is necessary to obtain fragments of <2 microns. This can be accomplished by a number of dispersion methods, for example, sonication of the extracellular matrix. Alternatively, the solubilized extracellular matrix can be fragmented within an acceptable range by enzyme digestion or treatment with chaotropic agents such as guanine hydrochloride that interferes with the three dimensional structure of the protein(s) to help break apart large fragments. Once the solubilized extracellular matrix is adequately fragmented to ensure even distribution and application within small diameter blood vessels, the mixture can be neutralized to a physiologic pH. By keeping the neutralized extracellular matrix at a temperature range of 4° C. to 8° C., re-polymerization will not occur. Re-polymerization will only occur when the mixture reaches a near-normothermic temperature.

Application of the ECM to the Vasculature

In order to uniformly apply the immunocloaking extracellular matrix to the luminal surfaces of the vasculature of a vascularized tissue or organ, the organ must first be established in a warm perfusion system using a substantially non-blood perfusate that is able to restore and support oxidative metabolism of the organ. Establishing the tissue or organ in a warm perfusion system involves isolating an organ, tissue or specific area of anatomy from the rest of the physiologic system by removing or interrupting the arterial source of blood feeding the desired tissue(s). Likewise, the venous outflow from the organ or section of anatomy is interrupted and the venous effluent is collected. If the tissue is completely excised from the body, then the enervation and lymphatics of the tissue(s) are also isolated. Next, the organ or tissue is flushed through the arterial system with the solution of the present invention at a temperature of about 25°-37° C. to remove blood and blood products. The organ is then placed in an exsanguinous metabolic support system and perfused with non-blood perfusion solution, for example as described in U.S. Pat. No. 6,642,045, while various parameters of the perfusion are monitored by the system and regulated as necessary to maintain adequate metabolism of the organ or tissue. Organ function is also monitored, for example, by collecting an organ product, such as urine or bile, and evaluating whether physical and chemical parameters of the organ product are within the range associated with normal function for that particular organ (see for example, U.S. Pat. No. 6,375,613, the contents of which are incorporated by reference.)

For purposes of the present method, the organ is perfused at a near-normothermic temperature using a non-blood perfusion solution for a time sufficient to restore oxidative metabolism and obtain NO-mediated vasodilation of the vasculature of the organ, particularly the microvessel bed, in order to avoid clogging the small diameter blood vessels with the extracellular matrix material once it is introduced into the organ. Without a continuous flux of NO and the resulting dilation, the immunocloaking material will clog the small diameter blood vessels. In contrast, with adequate support of NO-mediated vasodilation, the neutralized but still solubilized cold immunocloaking material can be uniformly applied to result in a continuous masking of the vascular endothelium along the vasculature (FIG. 1).

Establishment of Adequate Vasodilation Mediated By a Flux of NO

Maintenance of the organ in a warm perfusion system using a non-blood perfusion solution enables the monitoring of NO flux to determine when vasodilation of the vasculature is adequate and administration of the immunocloaking material is appropriate.

Adequate vasodilation is usually achieved after about 30-minutes from the time that perfusion is initiated and will be presumed, for example, when mean arterial pressures are in the range of about 32 mmHg to about 47 mmHg. Similarly, adequate vasodiation is usually accompanied by mean vascular flow rates in the range of about 90 cc/min to about 180 cc/min.

Immunocloaking material is infused into the organ or tissue at a rate of approximately 100 μg per minute. At a perfusion temperature of about 25° C. to 37° C., polymerization of the immunocloaking material will result in a uniform covering several nanometers in thickness without obstruction of the blood vessel lumen. This unobstructed distribution occurs also within the microvessel bed. The histologic findings indicate that at a dose range of 66 to 660 μg per gram of kidney, more than 90% of the blood vessels within a vascularized tissue or organ can be sufficiently and uniformly immunocloaked.

In order to obtain adequate and firm binding of the re-polymerized extracellular matrix to the surface of the vascular endothelium it is necessary to facilitate efficient integrin binding of the matrix via the RGD sequences within the immunocloaking material to the vascular endothelial cell family of integrins. To achieve this firm binding an adequate magnitude of oxidative metabolism must be maintained in the perfusing tissue or organ. A sufficient level of oxidative metabolism is necessary in order to facilitate the requisite translocation of the vascular endothelial cell integrins that are normally localized at the abluminal surfaces of the cells. The translocation occurs upon signal transduction initiated by the layering of the laminin components of the solubilized extracellular matrix preparation. With adequate oxidative metabolism as measured by oxygen consumption across the tissue or organ of >0.1 cc/min/g, the translocated integrins are expressed on the luminal surface of the vascular endothelium. This translocation of the surface integrins, in particular but not exclusively the β1 family of integrins, results in the firm binding of the re-polymerized extracellular matrix to the vascular luminal surfaces of the blood vessels within the tissue or organ. This firm binding persists following reimplantation and reperfusion. Following such reimplantation and reperfusion the re-polymerized extracellular matrix remains intact along the luminal surfaces within the vasculature for a minimum of 21 days rendering the tissues and organs nonimmunogenic and nonthrombogenic.

Competitive Binding Assay

A competitive binding assay was used to evaluate the binding capacity of each of the control and improved preparations of extracellular matrix material. Vascular endothelial cells were grown to confluence in tissue culture wells. The confluent monolayer was washed three times. The immunocloaking material prepared in accordance with the method of U.S. Pat. No. 5,643,712 was compared for binding efficiencies to the material produced by the method of the present invention. The testing was performed in triplicate with 100 μl of each preparation added to the confluent vascular endothelial cells. The extracellular matrix preparation were incubated for 30 minutes at 37° C. and then copiously washed to remove any unbound extracellular matrix material. The wells were then treated with anti-β1 integrin IgG and incubated again at 37° C. for 30 minutes. Following incubation, the wells were again copiously washed and a fluorescein tagged anti-IgG was added and the wells were again incubated for 30 minutes at 37° C. The labeled wells were then read using a PerkinElmer VICTOR2 multilabel counter. The wells treated with the extracellular matrix made using the process of the U.S. Pat. No. 5,643,712 contained significantly more fluorescence than the extracellular matrix produced by the method of the present invention. (Table 3)

Immunocloaking Mechanism of Protection

The extracellular matrix produced, processed and applied as described above results in protection from the recipient's immune response for a minimum of thirty days. The application of the immunocloaking extracellular matrix membrane prevents allorecognition by the recipient by preventing antigen presentation and T cell activation. To demonstrate the impact of extracellular matrix ability to immunocloak, human responding mononuclear cells (responders) were stimulated with autologous lymphocytes (negative controls) and untreated confluent monolayers of donor umbilical vein vascular endothelial cells (positive controls). The test groups consisted of the same confluent donor vascular endothelial cells that were immunocloaked with the extracellular matrix membrane of the present invention.

Early T cell activation was measured using CD4+, CD69+ detection by flow cytometry following 24 hours (n=10). Measurements were also made for the cytokines—IL-2, IL-6 and MIG using the Luminex xMap platform. In addition, following stimulation, supernatants were collected from each triplicate well and tested for additional cytokine and chemokine responses to evaluate antigen presentation. These cytokines and chemokines tested associated with antigen presentation included: IL-1β, TNF-α, MIP-1α and γ-IFN.

Immunocloaking of the vascular endothelial cells resulted in statistically significant inhibition of the cytokines and chemokines: IL-1β, IL-6, γ-IFN, IL-2, TNF-α, CD-69, MIG and MIP-1α ($p<0.005$) (FIG. 2). The finding of the inhibition of the cytokines produced by antigen presenting cells, MIP-1α, IL-1β, γ-IFN and TNF-α suggest that immunocloaking vascular endothelial cells with the extracellular matrix membrane of the present invention prevents antigen presentation. Since IL-1, γ-IFN and TNF-α are pro-inflammatory cytokines, the ability of the extracellular matrix barrier membrane to inhibit their release provides further evidence of the protective effect of immunocloaking. Similarly, the inhibition of markers of T cell activation, IL-6, IL-2, CD-69 and MIG suggest the blockade of T cell mediated responses when the vascular endothelial cells are immunocloaked with the membrane. It is reasonable to assume that the immunocloaking extracellular matrix membrane that prevents primary antigen recognition would also prevent endothelial cell activation. Preventing endothelial cell activation would likewise prevent the externalization of the pre-formed Weibel-Palade bodies that contain P-selectin adhesion molecules. Without a proinflammatory signal the multi-step leukocyte extravasation process would be adverted while the extracellular matrix membrane masks the allograft. The results of these immunologic screenings support the hypothesis that immunocloaking can be successfully used in an organ-specific manner to prevent the allorecognition that normally occurs upon reperfusion.

The present invention provides an optimized material and treatment that can be applied to the luminal surfaces within tissues and organs that renders the treated tissues nonimmunogenic and nonthrombogenic. The material and its application can be used treat an allograft, tissue engineered construct or a xenograft. Such an immunocloaking therapy can provide a window of protection that prevents the normal immune response to engraftment of a foreign tissue. This window of opportunity provides a period where tolerance induction protocols can be successfully applied.

Re-Application of the Extracellular Matrix Membrane

Following the period of immune protection where antigen presentation and T cell activation and proliferation is prevented, it is feasible to re-administer the extracellular matrix membrane therapy. As the barrier membrane provided by the bound re-polymerized extracellular matrix degrades, components of the membrane are exposed within the luminal surfaces. A purified laminin scaffolding can be re-applied via introduction into the intravascular space and will bind to the surface of the deteriorating immunocloaking material. This can be followed by application of the complete solubilized extracellular material. The new laminin scaffolding provides a substrate onto the deteriorating bound extracellular matrix membrane. The solubilized extracellular matrix that is maintained cold and neutralized can then be re-administered intravenously. The solubilized extracellular matrix preferentially binds to the new laminin scaffolding and results in a newly formed bound extracellular matrix membrane that provides further protection from immune rejection. The re-administration of the extracellular matrix immunocloaking membrane can be reapplied approximately every 21 days. This replacement therapy that is tissue- and organ-specific can substitute for the daily multi-drug immunosuppressive regimens that are needed today.

I claim:

1. An Arg-Gly-Asp (RGD)-enriched solubilized extracellular matrix isolated from cultured corneal endothelial cells (CEC) or human umbilical vascular endothelial cells (HUVECs), said matrix comprising protein content in the amount of 1-5 mg/ml of total ECM and having an RGD absorbance at 450 nm of 0.3 to 0.7, and a fragment size of less than 2 microns.

2. A composition comprising the solubilized extracelluar matrix of claim 1.

3. A method of modifying the immunogenicity and/or thrombogenicity of the luminal surfaces of the vasculature of a tissue or organ, the method comprising:

(a) establishing the organ or tissue to be modified in a warm perfusion system capable of supporting near normal oxidative metabolism of the organ or tissue;

(b) perfusing the organ or tissue with a non-blood perfusion solution comprising a component of the citric acid cycle selected from the group consisting of coenzyme A, flavin adenine dinucleotide (FAD), β-nicotinamide adenine dinucleotide (NAD or DPN), β-nicotinamide adenine dinucleotide phosphate (NADP$^+$ or TPN$^+$), and cocarboxylase, for a time sufficient for vasodilation to occur; and (c) introducing into the organ or tissue an Arg-Gly-Asp (RGD)-enriched solubilized extracellular matrix, isolated from cultured corneal endothelial cells (CEC) or human umbilical vascular endothelial cells (HUVECs), preparation comprising extracellular protein from endothelial cell cultures in the amount of 1-5 mg/ml and an RGD absorbance at 450 nm of 0.3 to 0.7 in an amount sufficient to substantially coat the luminal surfaces of the vasculature of the organ or tissue, wherein said solubilized extracellular matrix preparation renders the organ or tissue nonthrombogenic, and substantially nonimmunogenic.

4. The method of claim 3, wherein the amount sufficient to substantially coat the luminal surfaces of the vasculature of the organ or tissue to be modified is in the range of about 66 to about 660 µg/gram weight of organ or tissue.

5. The method of claim 3, wherein steps b) and c) are performed in a warm preservation system at a temperature in the range of about 22° C. to about 35° C.

6. The method of claim 3, wherein the extracellular matrix preparation is derived from human corneal endothelial cells.

7. A method for making an RGD-enriched solubilized extracelluar matrix composition, the method comprising:

(a) culturing endothelial cells to confluence in an endothelial cell culture medium comprising ascorbic acid, retinoic acid and a glucose concentration in the range of about 1 to about 10 mg/ml;

(b) decellularizing the culture to remove endothelial cells but leave the intact extracellular matrix;

(c) solubilizing the extracellular matrix by acidification in the cold; and (d) disrupting the solubilized extracellular matrix to ensure fragment size of <2 microns; and (e) recovering the RGD-enriched solubilized extracellular matrix, wherein said solubilized extracellular matrix isolated from cultured corneal endothelial cells (CEC) or human umbilical vascular endothelial cells (HUVECs), comprises extracellular protein from endothelial cells in the amount of 1-5 mg/ml, an RGD absorbance at 450 nm of 0.3 to 0.7 and a fragment size of less than 2 microns.

8. The method of claim 7, wherein the glucose concentration is between about 2.5 and about 7.5 mg/ml.

9. The method of claim 7, wherein the glucose concentration is between about 4 mg/ml and about 6 mg/ml.

10. The method of claim 7, wherein the glucose concentration is about 5 mg/ml.

11. The method of claim 7, wherein the ascorbic acid concentration is between about 10 and 30 µg/ml.

12. The method of claim 7, wherein the ascorbic acid concentration is about 20 µg/ml.

13. The method of claim 7, wherein the retinoic acid concentration is between about 100 to 200 µg/ml.

14. The method of claim 7, wherein the retinoic acid concentration is about 152 μg/ml.

\* \* \* \* \*